(12) United States Patent
Jackson

(10) Patent No.: US 7,837,716 B2
(45) Date of Patent: Nov. 23, 2010

(54) THREADFORM FOR MEDICAL IMPLANT CLOSURE

(76) Inventor: Roger P. Jackson, 4706 W. 86th St., Prairie Village, KS (US) 66207

( * ) Notice: Subject to any disclaimer, the term of this patent is extended or adjusted under 35 U.S.C. 154(b) by 550 days.

(21) Appl. No.: 10/964,156

(22) Filed: Oct. 13, 2004

(65) Prior Publication Data

US 2006/0079893 A1 Apr. 13, 2006

Related U.S. Application Data

(63) Continuation of application No. 09/644,777, filed on Aug. 23, 2000.

(51) Int. Cl.
*A61B 17/70* (2006.01)
(52) U.S. Cl. ...................... 606/278; 606/305
(58) Field of Classification Search ................ 606/278, 606/279, 305, 300, 330
See application file for complete search history.

(56) References Cited

U.S. PATENT DOCUMENTS

| | | |
|---|---|---|
| 3,640,416 A | 2/1972 | Temple |
| 4,041,939 A | 8/1977 | Hall |
| 4,653,486 A | 3/1987 | Coker |
| 4,707,001 A | 11/1987 | Johnson |
| 4,950,269 A | 8/1990 | Gaines, Jr. |
| 5,005,562 A | 4/1991 | Cotrel |
| 5,022,791 A | 6/1991 | Isler |
| 5,034,011 A | 7/1991 | Howland |
| 5,092,635 A | 3/1992 | DeLange et al. |
| 5,102,412 A | 4/1992 | Rogozinski |
| 5,147,363 A | 9/1992 | Harle |
| 5,275,601 A | 1/1994 | Gogolewski et al. |
| 5,306,275 A | 4/1994 | Bryan |
| 5,321,901 A | 6/1994 | Kelly |
| 5,358,289 A | 10/1994 | Banker et al. |
| 5,427,418 A | 6/1995 | Watts |
| 5,468,241 A | 11/1995 | Metz-Stavenhagen et al. |
| 5,474,555 A | 12/1995 | Puno et al. |
| 5,490,750 A | 2/1996 | Gundy |
| 5,499,892 A | 3/1996 | Reed |
| 5,507,745 A | 4/1996 | Logroscino et al. |
| 5,562,663 A | 10/1996 | Wisnewski et al. |
| 5,569,251 A | 10/1996 | Baker et al. |
| 5,601,553 A | 2/1997 | Trebing et al. |
| 5,607,304 A | 3/1997 | Bailey et al. |
| 5,607,425 A | 3/1997 | Rogozinski |
| 5,607,428 A | 3/1997 | Lin |
| 5,611,800 A | 3/1997 | Davis et al. |
| 5,628,740 A | 5/1997 | Mullane |
| 5,641,256 A | 6/1997 | Gundy |
| 5,643,261 A | 7/1997 | Schafer et al. |
| 5,662,652 A | 9/1997 | Schafer et al. |
| 5,662,653 A | 9/1997 | Songer et al. |

(Continued)

FOREIGN PATENT DOCUMENTS

DE 4425392 11/1995

(Continued)

*Primary Examiner*—Ralph A Lewis
(74) *Attorney, Agent, or Firm*—John C. McMahon

(57) ABSTRACT

A thread is located on a cylindrical closure for an open headed medical implant. The thread has a leading surface and a trailing surface that both slope rearwardly from an interior edge to an exterior edge thereof.

5 Claims, 2 Drawing Sheets

U.S. PATENT DOCUMENTS

| | | |
|---|---|---|
| 5,672,176 A | 9/1997 | Biederman et al. |
| 5,683,390 A | 11/1997 | Metz-Stavenhagen et al. |
| 5,697,929 A | 12/1997 | Mellinger |
| 5,711,709 A | 1/1998 | McCoy |
| 5,713,898 A | 2/1998 | Stucker et al. |
| 5,723,013 A | 3/1998 | Jeanson et al. |
| 5,725,527 A | 3/1998 | Biederman et al. |
| 5,728,098 A | 3/1998 | Sherman et al. |
| 5,733,286 A | 3/1998 | Errico et al. |
| 5,738,685 A | 4/1998 | Halm et al. |
| 5,741,254 A | 4/1998 | Henry et al. |
| 5,752,957 A | 5/1998 | Ralph et al. |
| 5,782,833 A | 7/1998 | Haider |
| 5,797,911 A | 8/1998 | Sherman et al. |
| 5,800,547 A | 9/1998 | Schafer et al. |
| 6,001,098 A | 12/1999 | Metz-Stavenhagen et al. |
| 6,063,090 A | 5/2000 | Schlapfer |
| 6,074,391 A | 6/2000 | Metz-Stavenhagen et al. |
| 6,077,262 A | 6/2000 | Schlapfer et al. |
| 6,117,137 A | 9/2000 | Halm et al. |
| 6,143,032 A | 11/2000 | Schafer et al. |
| 6,296,642 B1 * | 10/2001 | Morrison et al. .............. 606/61 |
| 6,402,757 B1 | 6/2002 | Moore et al. |
| 6,485,492 B1 | 11/2002 | Halm et al. |
| 6,540,749 B2 | 4/2003 | Schafer et al. |

FOREIGN PATENT DOCUMENTS

| | | |
|---|---|---|
| DE | 19509331 | 9/1996 |
| DE | 298 06 563 U1 | 7/1998 |
| DE | 29810798 | 12/1999 |
| DE | 19951145 | 5/2001 |
| EP | 0885598 | 12/1998 |
| WO | WO92/03100 | 3/1992 |
| WO | WO94/26191 | 11/1994 |

* cited by examiner

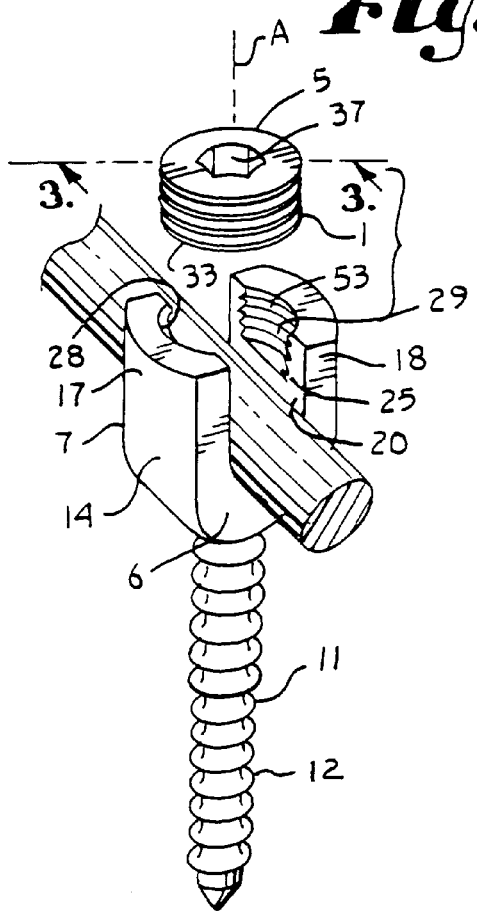
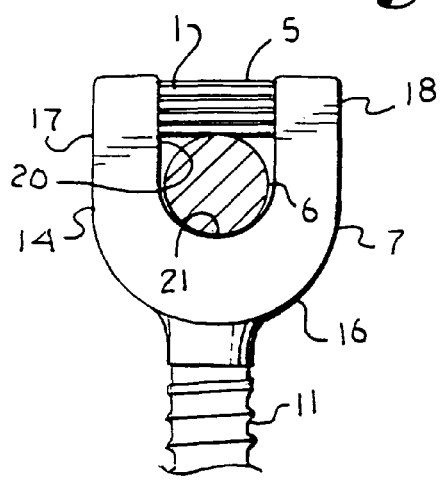
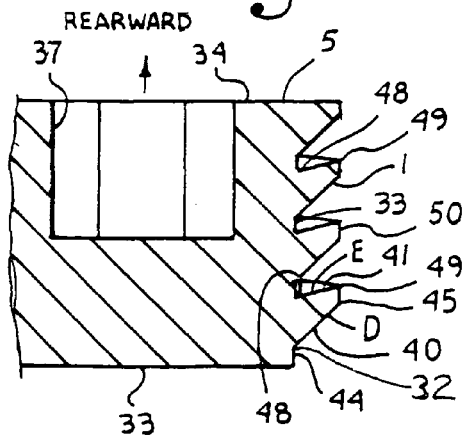

THREADFORM FOR MEDICAL IMPLANT CLOSURE

CROSS-REFERENCE TO RELATED APPLICATIONS

This application is a continuation of U.S. patent application Ser. No. 09/644,777, filed Aug. 23, 2000.

BACKGROUND OF THE INVENTION

The present invention is directed to a threadform for use in threadedly joining together two elements and, in particular, to a threadform for joining together medical implants. The threadform includes a leading surface and a trailing surface, both of which slant rearwardly and away from the direction of advancement from an inner edge to an outer edge thereof.

Medical implants present a number of problems to both surgeons installing implants and to engineers designing them. It is always desirable to have the implant be strong and unlikely to fail or break during usage. It is also desirable for the implant to be as small and lightweight as possible so that it is less intrusive on the patient. These are normally conflicting goals, and often difficult to resolve.

One particular type of implant presents special problems. In particular, spinal bone screws, hooks, etc. are used in many types of back surgery for repair of injury, disease or congenital defect. For example, spinal bone screws of this type are designed to have one end that inserts threadably into a vertebra and a head at an opposite end thereof. The head is designed to receive a rod or rod-like member which is then both captured in the head and locked in the head to prevent relative movement between the various elements subsequent to installation.

There are two different major types of bone screws and similar devices. The types are closed head and open head. The closed head devices are highly effective at capturing the rod since the rod is threaded through an opening in the head. Unfortunately, closed head devices are very difficult to work with in actual surgery as the spine is curved and the rods are also curved in order to follow the spine. Consequently, the more heads that the rod must pass through, the more difficult it is to thread it.

The second type of head is an open head wherein a channel is formed in the head and the rod is simply laid in an open channel. The channel is then closed with a closure. The open headed bone screws and related devices are much easier to use and in some situations must be used over the closed headed devices.

While the open headed devices are often necessary and often preferred for usage, there is a significant problem associated with them. That is, the open headed devices conventionally have two upstanding arms that are on opposite sides of a channel that receives the rod member. In order to lock the rod member in place, significant forces must be exerted on a relatively small device. The forces are required to provide enough torque to insure that the rod member is locked in place relative to the bone screw so that it does not move axially or rotationally therein. This typically requires torques on the order of 100 inch pounds.

Because the bone screws, hooks and the like are relatively small, the arms that extend upwardly at the head can be easily bent by radially outward directed forces due to the application of substantial forces required to lock the rod member. Historically, early closures were simple plugs that were threaded and which screwed into mating threads on the inside of each of the arms. However, conventionally threaded plugs push the arms radially outward upon the application of a significant amount of torque which ends up bending the arms sufficiently to allow the threads to disengage and the closure to fail. To counter this various engineering techniques were applied to allow the head to resist the spreading force. For example, the arms were significantly strengthened by increasing the width of the arms by many times. This had the unfortunate effect of substantially increasing the weight and the size of the implant, which was undesirable. Many prior art devices have also attempted to provide rings or some other type of structure that goes about the outside of the arms to better hold the arms in place while the center plug is installed. This additional structure has typically caused the locking strength of the plug being reduced which is undesirable. Also, the additional elements are unfavorable from a point of view of implants, as it typically desirable to maintain the number parts associated with the implants at a minimum.

Consequently, a lightweight and low profile closure plug was desired that resists spreading of the arms while also not requiring additional elements that circle around the outside of the arms so as to hold the arms in place.

SUMMARY OF THE INVENTION

A threaded closure for use in conjunction with an open headed medical implant wherein the thread associated with the closure exerts forces that draw the arms radially inward toward the closure rather than outward from the closure during installation. In this manner the arms do not spread substantially during installation of the closure under the torque required to lock a rod member within the head of the implant.

The thread is preferably helically wound about a cylindrical outer surface of the closure and preferably has an inner radius and outer radius that remain constant over substantially the entire length of the thread. The thread has both a leading surface and a trailing surface that have inner edges that are spaced from one another. Preferably the outer edges of the leading and trailing surfaces are in close proximity to one another such that the thread has a generally obtuse triangular shaped cross-section, with minor reduction or rounding at the outer tip.

Whereas in V-shaped thread forms, the leading surface slopes rearwardly from the inner edge and the trailing surface slopes frontwardly from the leading edge, and in buttress-type threads, the leading surface slopes rearwardly from the inner edge and the trailing surface slopes slightly frontwardly or has no slope, the thread of the present invention is such that both the leading surface and the trailing surface slope rearwardly with respect to the direction of advancement from the respective inner edges to outer edges thereof. That is, the intersections of a plane passing through an axis of rotation of the closure with the leading and trailing surfaces both slope rearwardly from the respective inner edges of the leading and trailing surfaces relative to the direction of advancement of the closure in the open-headed implant.

The inner facing surfaces of the arms are likewise threaded with a mating threadform that is sized and shaped to mate with the thread on the closure. The mating threadform on the implant arms is discontinuous between the arms.

Because of the configuration of the thread on the closure and the mating thread on the arms, forces applied to the closure, during installation of the closure between the arms, produce a reactive axial force on the arms of the implant, but also produce a somewhat inward force thereon. Therefore, the arms are urged toward the closure during installation rather than away from the closure during installation. In this manner the thread and mating thread function in a gripping manner between the opposed elements to hold them together, rather than force them apart.

OBJECTS AND ADVANTAGES OF THE INVENTION

Therefore, the objects of the present invention are: to provide a closure for an open headed lightweight and low profile medical implant wherein the implant has a pair of spaced arms and the closure closes between the arms; to provide such a closure which is threaded and which does not substantially space the arms during insertion, so as to reduce the likelihood of failure of the implant and closure system during use; to provide such a closure having a threadform that includes leading and trailing surfaces, both of which surfaces slope rearwardly from inner edges to outer edges thereof; to provide such a closure wherein the inner edges of both the trailing and leading surfaces have substantially constant radius over an entire length of the thread; to provide such a closure which can be installed at comparatively high torques so as to lock a rod member in the open head of the implant; and to provide such a closure and implant that are relatively easy to use and especially well adapted for the intended usage thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded perspective view of an open headed bone screw, rod and closure for the bone screw in accordance with the present invention.

FIG. 2 is a fragmentary side elevational view of the bone screw, rod and closure installed in the bone screw.

FIG. 3 is a fragmentary cross-sectional view of the closure, taken along line 3-3 of FIG. 1.

DETAILED DESCRIPTION OF THE INVENTION

Figure 4:
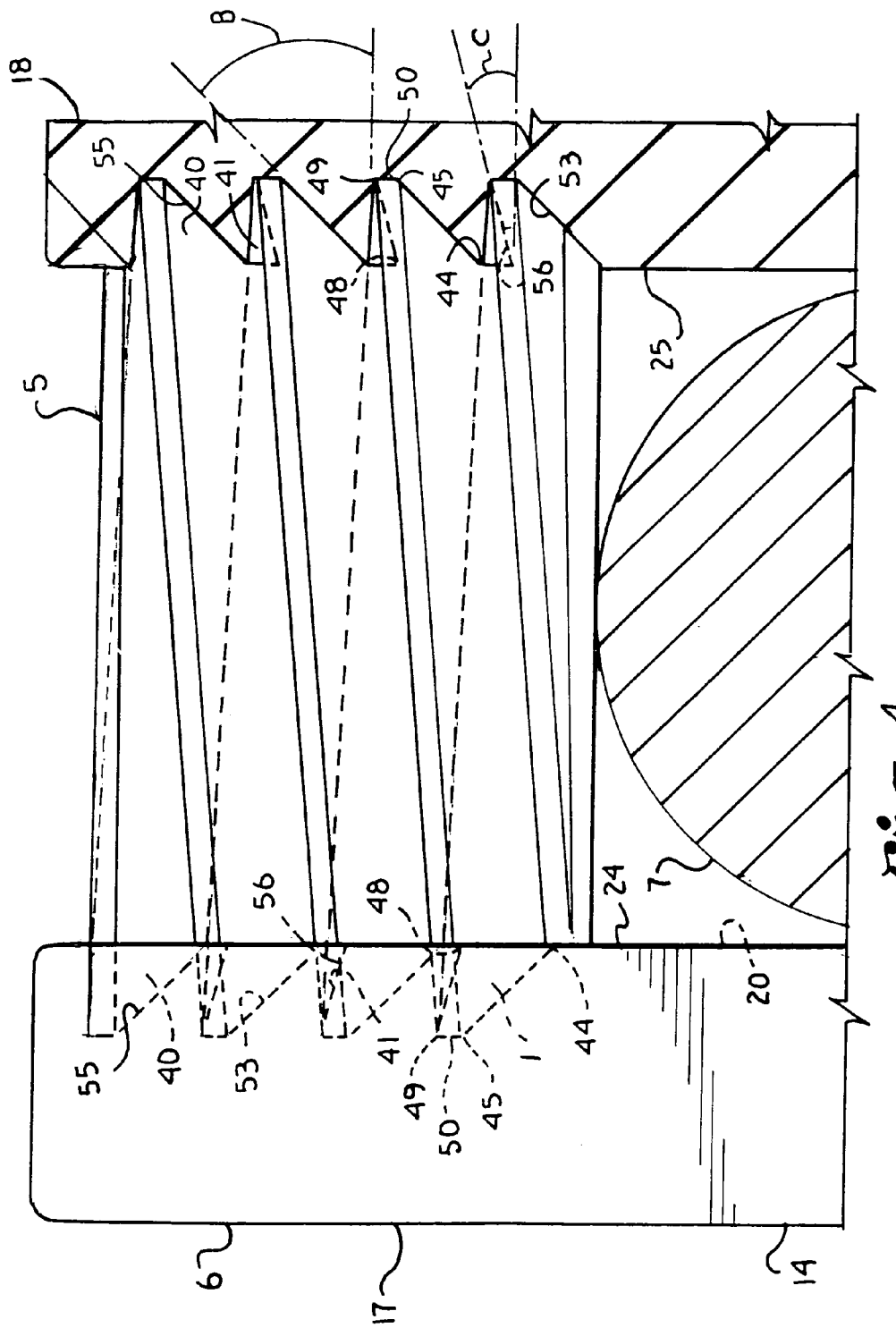
FIG. 4 is a highly enlarged and fragmentary side elevational view of the bone screw, rod and closure with a right hand arm of the bone screw shown in phantom lines in order to better illustrate features of the closure.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

The reference 1 generally indicates a thread form or thread in accordance with the present invention that is located on a medical implant closure 5 that is used in conjunction with a rod member 6 and an open headed medical implant 7.

Describing the elements in reverse order, the illustrated open headed medical implant 7 is a bone screw for use in spinal surgery. The implant 7 includes a shank 11 having a bone engaging and implantation thread 12 thereon. The implant 7 also includes an open head 14. The head 14 is U-shaped having a base 16 and a pair of upstanding spaced arms 17 and 18. The arms 17 and 18 are spaced by a channel 20 having a seat 21 at the bottom thereof. The arms 17 and 18 have facing surfaces 24 and 25 that are sides of the channel 20. Each of the surfaces 24 and 25 have facing threaded sections 28 and 29 respectively.

While the medical implant 7 shown here in is an open headed bone screw, it is foreseen that the present invention can be easily used and adapted with other types of open headed implants such as hooks and the like.

The rod member 6 is typically simply an elongated cylindrical rod which may be bent by benders to conform with the desired curvature of the spine. The rod member may be smooth or knurled. The rod member 6 may also include other types of similar structures such as connectors having a cylindrical or rod like nipple associated therewith for insertion into the bone screw head 14.

The illustrated closure 5 is a cylindrical shaped plug having a generally cylindrical shaped radially outer surface 32, a flat bottom 33 and a flat top 34. The closure 5 has an axis of rotation, generally indicated by the reference numeral A. The axis of rotation A is at the radial center of the closure 5. A bore 37 that is co-axial with the axis of rotation A extends through the top 34 and partially though the closure 5. The bore 37 is polyfaceted so as to have a hexagonal cross section such that closure 5 can be installed or removed with an allen type wrench that fits the bore 37.

Although a particular closure 5 has been illustrated herein, it is foreseen that the invention can be used in conjunction with plugs and set screws of various types and configurations. For example, the closure 5 may include a break off head for insertion and various types of structure for removal, as opposed to the bore 37. The closure 5 may also include structure to assist in engaging and securing the rod member 6, such as a depending point, a roughened under surface, or a cutting ring. Finally, although the closure of the present invention is illustrated in use in conjunction with an open headed implant, it is foreseen that the closure 5 could be utilized in conjuncture with closed bores, either as a plug or set screw.

The thread 1 winds about the outer surface 32 of the closure 5 in a generally helical pattern or configuration, which is typical of threads and can have various pitches, be counter-clockwise advanced or vary in most of the ways that conventional threads vary. The thread 1 has a leading surface 40 and a trailing surface 41. As used herein the terms leading and trailing refer to the direction of advancement of the closure 5 when used to close the implant 7 which is downward or in the direction of the rod member 6 in FIG. 4. In the illustrated embodiment, advancement is produced by clockwise rotation. The leading surface 40 has an inner edge 44 and an outer edge 45. The trailing surface 41 also has an inner edge 48 and an outer edge 49.

With reference to FIG. 3, the leading surface inner edge 44 and trailing surface inner edge 48 are substantially spaced. Both the leading surface inner edge 44 and trailing surface inner edge 48 have substantialably constant radius with respect to the axis of rotation A, preferably throughout the length of the thread 1 and at least throughout substantially most of the thread 1. The leading surface outer edge 45 and trailing surface outer edge 49 are closely spaced relative to one another and may be slightly relieved as shown so as to have a slight connecting wall 50 that decreases the sharpness of the thread 1 and increases the strength thereof. As can be seen in FIG. 3, the general shape of the cross section of the thread 1 is that of a obtuse triangle with the outer sharpened edge slightly reduced. It can also be seen that the intersection of the leading surface 40 and the trailing surface 41 with a plane passing through the axis of rotation A which is essentially what is shown in the front or closest surface shown in FIG. 3 both slope rearwardly, as indicated by the arrow shown FIG. 3 from inner edges 44 and 48 to outer edges 45 and 49 thereof.

The angle indicated by the reference numeral B is between the intersection D of a plane passing through the axis of rotation A and the leading surface 40 and a radius perpendicular to the axis of rotation A. The angle indicated by the reference numeral C is between the intersection E of a plane passing through the axis of rotation A and the trailing surface 41 and a radius perpendicular to the axis of rotation A. The angle B is substantially greater than the angle C. The angle C will normally be between about 1 and 45° with the preferred angle being between 5° and 20° and with the most preferred angle being between being 7 to 15°. Greater angles than 45° may be utilized, but the thread decreases in strength as the angle C increases which increases the likelihood that the thread may break in use. The key feature of the trailing surface 41 is that the surface 41 slopes rearwardly from inside to outside. The angle B will vary with desired thread strength and width of wall 50, but will always be greater than angle C. Preferably the angle B is in the range from 30° to 70° and it is preferred that the angle B be in the range from 40° to 50°. In the illustrated embodiment angle B is approximately 45° and angle C is approximately 15°.

As is best seen in FIG. 4, the threaded sections 28 and 29 of the arms 17 and 18 respectively are provided with a threadform 53 that is sized and shaped to threadedly receive the thread 1. The threadform 53 is discontinuous, as it extends over the threaded sections 28 and 29. The threadform 53 has a first surface 55 that abuts against the leading surface 40 and a second surface 56 that abuts against the trailing surface 41 during use. It is noted that as torque is applied to closure 5 in a clockwise manner so as to advance the closure 5 in the implant 7, the trailing surface 41 engages and pushes against the second surface 56 associated with implant 7. The force exerted on the closure 5 by this process is countered by a reactive force acting on the implant 7 that has a first component that is axial, that is parallel to the axis of rotation of the closure 5, and second component that has a radial inward vector, that is toward the axis of rotation of the closure 5. The surfaces 40 and 41 are non parallel to each other.

It is foreseen that the thread 1 can be continuous or discontinuous, as is threadform 53.

It is to be understood that while certain forms of the present invention have been illustrated and described herein, it is not to be limited to the specific forms or arrangement of parts described and shown.

What is claimed and desired to be secured by Letters Patent is as follows:

1. A bone screw apparatus for securing a spinal implant rod to a patient's vertebra; said apparatus comprising:
   a) a bone screw shank adapted to be implanted into the vertebra;
   b) a head secured to the shank during usage and having a pair of spaced and upstanding arms forming a channel therebetween with said channel being sized and shaped to receive the rod;
   c) each of the arms having an inner surface with a discontinuous and aligned helically wound first threadform on each of the arm's inner surfaces; said first threadform having a lower surface nearest said shank and an upper surface; said head having an axis of rotation; said first threadform lower surface having a vertical cross section with a first angle of inclination relative to a radius perpendicular to said axis in a range from 30° to 70° and said first threadform upper surface having a vertical cross section with a second angle of inclination relative to a radius perpendicular to said axis that is always less than said first angle and is within a range of between 1° and 45° with respect to said axis; said first threadform lower surface having a first outer edge and said first threadform upper surface having a second outer edge spaced from said first outer edge; said first threadform having a third surface connecting said first and second outer edges; said third surface joining the lower surface first outer edge and the upper surface second outer edge such that the first outer edge is substantially spaced below the second outer edge; both of said first threadform lower and upper surfaces being sloped in the same direction and said first threadform lower and upper surfaces being sloped both radially outwardly and upwardly relative to said axis, wherein a third angle defined by the upper and third surfaces is less than 90°; and
   d) a closure sized and shaped to close said channel after placement of the rod in the channel; said closure including a cylindrical body and a generally continuous helically wound threadform thereon that wraps on an outer surface of the body about said axis; said second threadform being sized and shaped to thread into and snugly mate with said first threadform upon joining and rotation of said closure between said arms; said closure including removal structure to provide for removal of the closure after inserting between the arms.

2. The apparatus according to claim 1 wherein:
   a) said first angle is in a range from 40° to 50°; and
   b) said second angle is in a range from 5° to 20°.

3. The apparatus according to claim 1 wherein:
   a) said first angle is about 45°; and
   b) said second angle is about 15°.

4. A bone screw apparatus for securing a spinal implant rod to a patient's vertebra; said apparatus comprising:
   a) a bone screw shank adapted to be implanted into the vertebra;
   b) a head secured to the shank during usage and having a pair of spaced and upstanding arms forming a channel therebetween with said channel being sized and shaped to receive the rod;
   c) each of the arms having an inner surface with a discontinuous and aligned helically wound first threadform on each of the arm's inner surfaces; said first threadform having a lower surface nearest said shank and an upper surface; said head having an axis of rotation; said first threadform lower surface having a vertical cross section with a first angle of inclination relative to a radius perpendicular to said axis in a range from 30° to 70° and said first threadform upper surface having a vertical cross section with a second angle of inclination relative to a radius perpendicular to said axis that is always less than said first angle and is within a range of between 1° and 45° with respect to said axis; said lower surface having a first outer edge and said upper surface having a second outer edge spaced from said first outer edge with the first outer edge being substantially vertically spaced below the second outer edge; said first threadform having a third surface connecting said first and second outer edges; both of said upper and lower surfaces being sloped in the same direction and both being sloped both radially outwardly and upwardly relative to said axis; and wherein said upper and third surfaces define a third angle of less than 90°; and d) a closure sized and shaped to close said channel after placement of the rod in the channel; said closure including a cylindrical body and a generally continuous helically wound threadform thereon that wraps around on an outer surface of the body about said axis; said second threadform being sized and shaped to thread into and snugly mate with said first threadform upon joining and rotation of said closure between said arms; said closure including removal structure to provide for removal of the closure after inserting between the arms.

5. A bone screw apparatus for securing a spinal implant rod to a patient's vertebra; said apparatus comprising:
  a) a bone screw shank adapted to be implanted into the vertebra;
  b) a head secured to the shank during usage and having a pair of spaced and upstanding arms forming a channel therebetween with said channel being sized and shaped to receive the rod;
  c) each of the arms having an inner surface with a discontinuous and aligned helically wound first threadform on each of the arm's inner surfaces; said first threadform having a lower surface nearest said shank and an upper surface; said head having an axis of rotation; said first threadform lower surface having a vertical cross section with a first angle of inclination relative to a radius perpendicular to said axis in a range from 30° to 70° and said first threadform upper surface having a vertical cross section with a second angle of inclination relative to a radius perpendicular to said axis that is always less than said first angle and is within a range of between 1° and 45° with respect to said axis; said lower surface having a first outer edge and said upper surface having a second outer edge spaced from said first outer edge; said first threadform having a third surface connecting said first and second outer edges; said third surface joining the first and second outer edges and with the first outer edge being vertically located beneath the second outer edge both of said upper and lower surfaces being sloped in the same direction and both being sloped both radially outwardly and upwardly relative to said axis; and wherein a third angle defined by the upper and third surfaces is less than 90°; and
  d) a closure sized and shaped to close said channel after placement of the rod in the channel; said closure including a cylindrical body and a generally continuous helically wound threadform thereon that wraps around on an outer surface of the body about said axis; said second threadform being sized and shaped to thread into and snugly mate with said first threadform upon joining and rotation of said closure between said arms; said closure including removal structure to provide for removal of the closure after inserting between the arms.

\* \* \* \* \*